United States Patent [19]
Larson

[11] Patent Number: 5,907,784
[45] Date of Patent: May 25, 1999

[54] METHOD OF MAKING MULTI-LAYER GATE STRUCTURE WITH DIFFERENT STOICHIOMETRY SILICIDE LAYERS

[75] Inventor: William L. Larson, Eden Prairie, Minn.

[73] Assignee: Cypress Semiconductor, San Jose, Calif.

[21] Appl. No.: 08/799,833

[22] Filed: Feb. 13, 1997

Related U.S. Application Data

[62] Division of application No. 08/606,577, Feb. 26, 1996, Pat. No. 5,635,765.
[51] Int. Cl.⁶ .................... H01L 21/3205; H01L 21/4763
[52] U.S. Cl. ............................................ 438/592; 438/683
[58] Field of Search ............................ 257/413; 438/592, 438/683

[56] References Cited

U.S. PATENT DOCUMENTS

| | | | |
|---|---|---|---|
| 4,816,879 | 3/1989 | Ellwanger | 375/15 |
| 4,872,050 | 10/1989 | Okamoto et al. | 357/71 |
| 4,877,755 | 10/1989 | Rodder . | |
| 4,886,764 | 12/1989 | Miller et al. . | |
| 4,946,803 | 8/1990 | Ellwanger | 437/175 |
| 5,010,037 | 4/1991 | Lin et al. | 437/200 |
| 5,221,853 | 6/1993 | Joshi et al. | 257/384 |
| 5,723,893 | 3/1998 | Yu et al. | 257/413 |
| 5,776,822 | 7/1998 | Fujii et al. | 438/586 |
| 5,780,361 | 7/1998 | Inoue | 438/683 |

OTHER PUBLICATIONS

Tungsten Silicide Formation From Sequentially Sputtered Tungsten And Silicon Films—J. M. Molarius, et al—Elsevier Science Publishers B.V. ©1991, pp. 383–390.
Lanthanum Silicide Formation In Thin La–Si Multilayer Films—C.C. Hsu, et al, vol. 41/Nos. 4–6/pp. 1425 to 1427/1990.
Interfacial Reactions and Thermal Stability Of Ultrahigh Vacuum Deposited Multilayered Mo/Si Structures—J. M. Liang et al—J. Appl. Phys. 79 (8), Apr. 15, 1996, pp. 4072–4077.
Examples For The Improvements In AES Depth Profiling Of Multilayer Thin Film Systems By Application Of Factor Analysis Data Evaluation—U. Scheithauer, © Springer–Verlag 1995, pp. 464–467.
Structure And Magnetism of Fe/Si Multilayers Grown By Ion–Beam sputtering—A. Chaiker et al, vol. 53, No. 9, pp. 5518–5529—Mar. 1, 1996.
Formation Of Amorphous And Crystalline Phases, And Phase Transition By Solid–State Reaction in Zr/Si Multilayer Thin Films—Jae–Yeob Shim et al, © 1995 Elsevier Science S.A., pp. 102–107.
Characterization Of The Titanium Silicon Two/Si Interface In Titanium Disilicide Films On Silicon, Formed By Deposition Of Alternate Titanium–Layers And Annealing—P. Revva et al, J. Appl. Phys. 75 (9), May 1, 1994, pp. 4533–4538.
Profiles And Chemistry Effects In Polysilicon And Tungsten Silicide EPROM "Stack" Etching—Daniel L. Flamm, et al, 24/SPIE vol. 1803 (1992), pp. 24–29.

(List continued on next page.)

*Primary Examiner*—Richard A. Booth
*Attorney, Agent, or Firm*—Maiorana & Acosta, P.C.

[57] ABSTRACT

A method of forming a multi-layer silicide gate structure for a MOS type semiconductor device that includes the processing steps of first providing a substrate, then depositing a gate oxide layer on the substrate, then depositing a first refractory metal silicide layer which has a first stoichometry on the gate oxide layer, and finally depositing a second refractory metal silicide layer which has a second stoichometry different than the first stoichometry on the first deposited refractory metal silicide layer.

19 Claims, 1 Drawing Sheet

```
30

36 ──   LAYER II    Si/W = 2.4/1.0

32 ──   LAYER I     Si/W = 2.0/1.0

34 ──        GATE OXIDE
```

OTHER PUBLICATIONS

Formation OF Sm Silicides on Si(111): Composition And Epitaxy—C. Wigren, et al, © 1993 Elsevier Science Publishers B.V., pp. 254–259.

Initial Evolution Of Cobalt Silicides In The Cobalt/Amorphous–Silicon Thin Film System—Hideo Miura, et al, Mat. Res. Soc. Symp. Proc. vol. 230, © 1992 Materials Research Society, pp. 139–144.

Initial Sequence And Kinetics Of Silicide Formation In Cobalt/Amorphous–Silicon Multilayer Thin Films—H. Mirua, et al, J. Appl. Phys. 70 (8), Oct. 15, 1991, pp. 4287–4294.

Silicide Formation By Solid State Reaction Of Mo–Ni And Mo–Co Films With Si(100)*—R. S. Rastogi, et al, © Elsevier Sequoia/Printed in the Netherlands, pp. 107–112, Thin Solid Films, 1991.

Formation Of $TiSi_2$ From Titanium and Amorphous Silicon Layers For Local Interconnect Technology—A. A. Bos, et al, © Elsevier Sequoia/Printed in the Netherlands, pp. 169–178, Thin Solid Films, 1991.

Microstructural Aspects Of Nickel Silicide Formation In Evaporated Nickel–Silicon Multilayer Thin Films—Karen Holloway et al, Mat. Res. Soc. Symp. Proc. vol. 159. © 1990 Materials Research Society, pp. 153–157.

Interdiffusion And Short–Range Order In Amorphous Ta–Si Multilayer Structures—H. L. Meyerheim et al., J. Appl. Phys. 68 (6), Sep. 15, 1990, pp. 2694–2701.

Thermally Induced Structural Modification of Mo–Si Multilayers—D. G. Stearns et al., J. Appl. Phys. 67 (5), Mar. 1, 1990, pp. 2415–2427.

Fabrication of Superlattice Structures By Plasma Controlled Magnetron Sputtering*—T. Hata et al., © Elsevier Sequoia/Printed in the Netherlands, pp. 467–473, Thin Solid Films, 1988.

Stresses In Sputtered Ti–Si Multilayers And Polycrystalling Silicide Films—P. J. J. Wessels, et al., J. Appl. Phys. 63 (10), May 15, 1988, pp. 4979–4982.

Interfacial Reactions In Titanium—Silicon Multilayers—Karen Holloway et al, Mat. Res. Soc. Symp. Proc. Vo. 77. © 1987 Materials Research Society; pp. 357–362.

$Wsi_x$ Formation in W–Si Multilayers—S. Eicher et al., Can J. Phys. vol. 65, 1987, pp. 868–871.

Formation Of Ion Beam Mixed Silicides On Si (100) At Elevated Substrate Temperatures—D. Fathy, et al., J. Appl. Phys. 58 (1), Jul. 1, 1985, pp. 297–301.

Pt–Ni Bilayers On n–Type Silicon: Metallurgical And Electrical Behavior—S. Mantovani, et al, J. Appl. Phys. 55 (4), Feb. 15, 1984, pp. 899–9086.

Taper Etching Of The Thermal Oxide Layer—Y. I. Chio, et al., Lee Proceedings, vol. 133, Pt. 1, No. 1, Feb., 1986, pp. 13–17.

Titanium Silicidation Characteristics of the a–Si/Ti/a–Si Multilayer By Rapid Thermal Annealing, Hyung Sup Yoon et al, New Physics, Vo. 30, No. 2, Apr. 1990, pp. 180–185.

Thermally Stimulated Interactions In Bilayers And Multilayers Containing Ni And Si During A Temperature Ramp—A. Cvelbar, et al., Informacije MIDEM 25(1995)3, pp. 196–204.

Silicide Formation Resulting From The Interfacial Reaction Of Silicon And Thin Films Of Ir–V Alloys And Bilayers—M. Eizenberg, Department of Materials Engineering and Solid State Institute, Technion–Israel Institute of Technology, Haifa, pp. 483–495, 1982.

(PRIOR ART)
FIG.1A
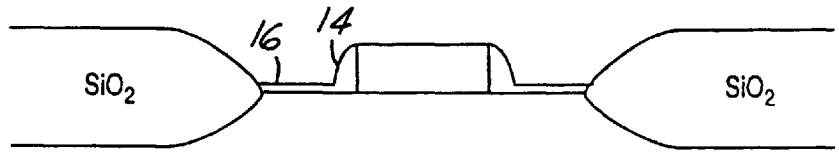
(PRIOR ART)
FIG.1B
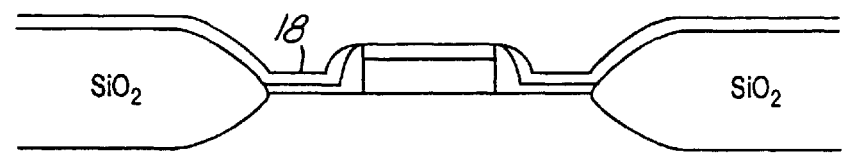
(PRIOR ART)
FIG.1C
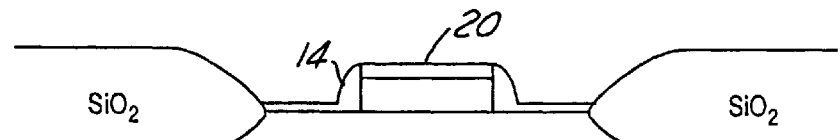
(PRIOR ART)
FIG.1D
| 30 | | |
|---|---|---|
| 36 — | LAYER II | Si/W = 2.4/1.0 |
| 32 — | LAYER I | Si/W = 2.0/1.0 |
| 34 — | GATE OXIDE | |
FIG.2

5,907,784

METHOD OF MAKING MULTI-LAYER GATE STRUCTURE WITH DIFFERENT STOICHIOMETRY SILICIDE LAYERS

This is a divisional of copending application Ser. No. 08/606,577 filed on Feb. 26, 1996 now U.S Pat. No. 5,635,765.

FIELD OF THE INVENTION

The present invention generally relates to a method of forming a multi-layer gate structure and the gate structure formed thereby and more particularly, related to a method of forming a multi-layer gate structure from a refractory metal silicide for use in a MOSFET device and the gate structure formed thereby.

BACKGROUND OF THE INVENTION

Traditionally, polysilicon layers have been used for the gates of transistors or as interconnect layers. In order to reduce the high resistance of polysilicon, doped polysilicon is sometimes used in those applications. However, even though the sheet resistance of doped polysilicon is reduced, it is still higher than desired, i.e., between 20 and 40 ohm/square. When the doped polysilicon is used as a long distance conductor, the polysilicon wire can represent a significant delay in transmission.

One method to improve the sheet resistance of doped polysilicon in gate applications that does not require additional processing steps, i.e. does not require additional masking steps is to reduce the polysilicon resistance by combining it with a refractory metal. In recent years, metal silicide films such as tungsten silicide and titanium silicide have been used to replace doped polysilicon films as the gate in MOSFET integrated circuits. The driving force behind this change is the need to reduce the resistivity of the polysilicon gate which in turn reduces the RC time constant of signal propagation. A much improved sheet resistance in the order of 1 to 5 ohm/square may be obtained. The process is frequently called the silicide gate approach. Silicides are mechanically strong and can be dry etched in plasma reactors. One of the more frequently used silicide, tantalum silicide is stable throughout standard processing temperatures and has the advantage that it can be retrofitted into existing fabrication processes. Silicide can also be used in a sandwiched structure of polysilicon commonly known as a polycide approach. The net effect of using a silicide gate is to reduce the second layer interconnect resistance and to allow the gate to be used as a moderate long-distance interconnect. Silicide is increasingly used in semiconductor fabrication processes to reduce the resistance of both gate and source/drain conductors.

Silicide formation between a silicon and a refractory metal can be accomplished by several means. For instance, silicide s can be formed by depositing a refractory metal layer on an existing polysilicon layer and then forming a silicide at its interface by annealing the two layers together at a sufficiently high temperature. Another method of forming silicide s is to deposit the silicide through sputter deposition from a refractory metal silicide target. Still another method of forming silicide s is the use of a chemical vapor deposition technique utilizing gaseous reactants that contain both the refractory metal and the silicon.

A conventional method for producing silicide films is shown in FIGS. 1A through 1D. On a silicon substrate 10, a layer of polysilicon 12 is first deposited and patterned as shown in FIG. 1A. Outside spacers 14 are then formed and a thin oxide layer 16 is grown in the active source/drain areas as shown in FIG. 1B. A refractory metal 18 such as titanium or tungsten which will subsequently form the silicide is then deposited on top of the oxide. Upon heating in a reducing environment, the metal reacts with the exposed silicon to form a stoichiometric silicide such as $TiSi_2$ or $WSi_2$ as shown in FIG. 1C. The metal 18 does not react where it is in contact with silicon dioxide and is removed in an etching process which etches the metal but not the silicide. This is shown in FIG. 1D. In this method, the silicide formed is stoichiometric and has a thickness that is determined by the available amount of the reactants, i.e., either the silicon thickness or more commonly the thickness of the deposited metal layer. This forms a silicide composed entirely of a single stoichiometry. The drawbacks of this method is that the metal silicide formed may have undesirable side effects such as typically, high stress, poor oxidation resistance, poor etchability and high contact resistance with other materials.

It is therefore an object of the present invention to provide a multi-layer gate structure and a method of such preparation for a MOS type semiconductor device that does not have the shortcomings and drawbacks of the prior art silicide gate structure or method of preparation.

It is another object of the present invention to provide a multi-layer silicide gate structure for a MOS type semiconductor device and a method of preparation that involves at least two deposition steps of refractory metal silicide wherein the stoichometry of each layer is different from the other.

It is a further object of the present invention to provide a multi-layer silicide gate structure for a MOS type semiconductor device and a method of such preparation that involves the deposition of a first refractory metal silicide layer that has a first stoichometry, and the deposition of a second refractory metal silicide layer that has a second stoichometry different than the first stoichometry.

It is another further object of the present invention to provide a multi-layer silicide gate structure for a MOS type semiconductor device and a method of such preparation that can be carried out on a silicon substrate in a chemical vapor deposition process.

It is yet another object of the present invention to provide a method of forming a multi-layer silicide gate structure for a MOS type semiconductor device and a method of such preparation where the refractory metal used is tungsten, titanium, tantalum and molydenum.

It is still another object of the present invention to provide a multi-layer silicide gate structure for a MOSFET device and a method of such preparation by a chemical vapor deposition process wherein a reactant gas of $SiH_4$ or $SiCl_2H_2$ is used.

SUMMARY OF THE INVENTION

In accordance with the present invention a multi-layer silicide gate structure for a MOS type semiconductor device and a method of such preparation are provided.

In the preferred embodiment, a multi-layer silicide gate structure for use in a MOS type semiconductor device is provided which includes a substrate layer, a gate oxide layer, a first refractory metal silicide layer that has a first stoichometry deposited on the gate oxide layer, and a second refractory metal silicide layer that has a second stoichometry different than the first stoichometry deposited on the first refractory metal silicide layer. The refractory metal utilized to form the metal silicide gate can be selected from tungsten, titanium, tantalum and molydenum. The substrate layer is normally a silicon substrate. In this preferred embodiment, the first stoichometry of the silicon/refractory metal is between about 2.0:1 and about 2.2:1. The second stoichometry of the silicon/refractory metal is higher than the first stoichometry, i.e. in the range between about 2.3:1 and about 2.5:1.

The present invention is further directed to a method of forming a multi-layer silicide gate structure for a MOS type semiconducter device that can be carried out by the processing steps of first providing a substrate, then depositing a gate oxide layer on the substrate, then depositing a first refractory metal silicide layer that has a first stoichometry on the gate oxide layer, and finally depositing a second refractory metal silicide layer that has a second stoichometry different than the first stoichometry on the first refractory metal silicide layer. The deposition process of the refractory metal silicide can be conducted in a chemical vapor deposition chamber by the reactant gasses of $SiH_4$ or $SiCl_2H_2$. The present invention method is therefore capable of depositing a silicide film that has a stoichometry which varies as a function of thickness of the film so that different parts of the film can be optimized for a specific function. For instance, the first layer deposited on the gate oxide can have a smaller stoichometric ratio to achieve a minimum film resistivity, while the second layer deposited may have a larger stoichometric ratio of silicon/refractory metal and thus a higher silicon content for improved oxidation resistance. The contact resistance to a second layer of polysilicon can also be improved due to the reduced levels of tungsten oxide at the interface.

The present invention multi-layer silicide gate structure may further include a third or fourth refractory metal silicide layer on top of the first and second refractory metal silicide layers. Each additional layer may have the same or different stoichometry than the first and the second layer such that special functions and the, consequently, optimal properties of the gate structure can be achieved.

BRIEF DESCRIPTION OF THE DRAWINGS

Other objects, features, and advantages of the present invention will become apparent upon consideration of the specification and the appended drawings, in which:

FIGS. 1A–1D are enlarged cross-sectional views of a gate structure constructed by a prior art deposition method wherein a tungsten layer is that deposited on a polysilicon layer and then heat annealed to form a silicide layer.

FIG. 2 is an enlarged cross-sectional view of a gate structure constructed according to the present invention method.

DETAILED DESCRIPTION OF THE PREFERRED AND THE ALTERNATE EMBODIMENTS

The present invention provides a multi-layer silicide gate structure for a MOS type semiconductor device that is constructed of multiple layers of refractory metal silicide having different stoichometry and therefore different physical properties. The electrical properties of the gate structure can be optimized by customizing each layer for a specific function desired.

Generally, the present invention overcomes the drawbacks and disadvantages of the prior art gate structures by depositing a refractory metal silicide film that has a stoichometry which varies as a function of the gate thickness so that different parts of the film can be optimized for a specific function. This is achieved by utilizing a method of chemical vapor deposition to deposit refractory metal silicide films. For instance, the stoichiometric or ideal silicon to tungsten ratio for tungsten silicide is 2:1. By increasing the flow rate of a silicon-containing reactant gas, such as $SiH_4$ or $SiClH_2$, the stoichiometric ratio can be increased to as high as 3:1. In particular, the ratio can be changed as a function of the thickness of the film. FIG. 2 illustrates an example of a two-layer tungsten silicide gate structure 30. A polycide structure is also possible, whereby a layer of doped polysilicon is deposited on the gate oxide, 34, prior to deposition of Layer I of the metal silicide film, 34.

The bottom layer 32 which is deposited on a gate oxide layer 34 has a silicon-tungsten ratio of 2:1. The layer is deposited by typically flowing a reactant gas of $SiCl_2H_2$ a refractory metal-containing reactant gas such as $WF_6$ at a volume ratio of approximately 40:1 into a reaction chamber of CVD. After the tungsten silicide film is formed, it is annealed in a furnace at between 900° C. and 1050° C. for a period of time between 30 and 90 minutes. The annealing process can also be carried out by a rapid thermal annealing technique in an inert gas environment in between 10 and 90 seconds. When oxidization of the top surface layer is desired, an oxygen environment can be used instead of the inert gas environment. The tungsten silicide film thus obtained has a film resistivity (or sheet resistance) at less than 4 ohm/square. The chamber pressure during the deposition is typically less than 10 Torr conducted in a CVD machine such as those manufactured by Applied Materials Inc. under the trade name of Centura®. In a similar process where titanium silicide film is deposited, a lower film resistivity of less than 1.5 ohm/square can be obtained.

The upper layer 36 shown in FIG. 2 is deposited with a higher silicon content at a silicon/tungsten ratio of 2.4:1. The higher silicon ratio improves the oxidation characteristics of the film when it is exposed to a high temperature oxidizing environment.

It has been noted that improved contact resistance to a second layer of polysilicon can also be achieved due to the reduced levels of tungsten oxide at the interface. In the two-layer structure illustrated in FIG. 2, the bottom layer can suitably have a stoichiometric ratio between about 2.0:1 and about 2.2:1 while the upper layer can suitably have a stoichiometric ratio between about 2.3:1 and about 2.5:1. In the case of tungsten silicide films, the total film thickness is approximately 2000 Å±1000 Å.

In the case where a polycide structure is used the polysilicon film thickness in typically 1000±500 Å thick and doped with phosphorus arsenic or boron with a concentration from $1E19$ $cm^{-3}$ to $5E20$ $cm^{-3}$.

It should be noted that while the present invention as described above in the preferred embodiment is illustrated with two layers of refractory metal silicide in the gate structure, a larger number of layers can also be constructed and be suitably used in such gate structures. For instance, the additional layers may have thermal coefficients of expansion that matches those of the first and the second refractory metal silicide layer such that a desirable stress-free structure can be obtained.

While the present invention has been described in an illustrative manner, it should be understood that the terminology used is intended to be in a nature of words of description rather than of limitation.

Furthermore, while the present invention has been described in terms of a preferred and an alternate embodiment thereof, it is to be appreciated that those skilled in the art will readily apply these teachings to other possible variations of the invention.

The embodiments of the invention in which an exclusive property or privilege is claimed are defined as follows:

1. A method of forming a multi-layer silicide gate structure for a MOS type semiconductor device comprising the steps of:

providing a substrate, depositing a gate oxide layer on the substrate, depositing a first refractory metal silicide layer having a first stoichometry on said gate oxide layer, and depositing a second refractory metal silicide layer having a second stoichometry different than said first stoichometry on said first refractory metal silicide layer.

2. A method according to claim 1, wherein said substrate is a silicon substrate.

3. A method according to claim 1, wherein a refractory metal of said first or second refractory metal silicide is a member selected from the group consisting of tungsten, titanium, tantalum and molybdenum.

4. A method according to claim 1, wherein said deposition step for said refractory metal silicide is conducted in a chemical vapor deposition chamber.

5. A method according to claim 1, wherein at least one of said refractory metal silicide deposition steps are conducted in a chemical vapor deposition chamber by flowing in a reactant gas of $SiH_4$ or $SiCl_2H_2$.

6. A method according to claim 1, wherein said first stoichometry of said silicon/refractory metal is between about 2.0:1 and about 2.2:1.

7. A method according to claim 6, wherein said second stoichometry of said silicon/refractory metal is higher than said first stoichometry.

8. A method according to claim 1, wherein said second stoichometry of said silicon/refractory metal is between about 2.3:1 and about 2.5:1.

9. A method according to claim 1, wherein said first and said second stoichometry of said silicon/refractory metal are between about 2.0:1 and about 2.2:1 and between about 2.3:1 and about 2.5:1, respectively.

10. A method according to claim 1, further comprising the step of depositing a third layer of refractory metal silicide on top of said second layer of refractory metal silicide, said third layer of refractory metal silicide having a third stoichometry that is different than said first and said second stoichometry.

11. A method of forming a multi-layer gate structure for a MOSFET device by a chemical vapor deposition process comprising the steps of:

providing a substrate, depositing a gate oxide layer, depositing a first refractory metal silicide layer at a first flow rate of a silicon-containing reactant gas and at a second flow rate of a refractory metal-containing reactant gas, and depositing a second refractory metal silicide layer on top of said first refractory metal silicide layer at a third flow rate of a silicon-containing reactant gas and at a fourth flow rate of a refractory metal-containing reactant gas, said third flow rate is higher than said first flow rate used in depositing said first refractory metal silicide layer.

12. A method according to claim 11, wherein said first refractory metal silicide layer has improved film resistivity relative to doped polysilicon having a sheet resistance between 20 and 40 ohms/square and said second refractory metal silicide layer has improved oxidation resistance relative to a refractory metal silicide having a stoichometry of silicon/refractory metal of 2:1.

13. A method according to claim 11, wherein said first refractory metal silicide layer has a stoichometry of silicon/refractory metal of between about 2.0:1 and about 2.2:1, and said second refractory metal silicide layer has a stoichometry of silicon/refractory metal of between about 2.3:1 and about 2.5:1.

14. A method according to claim 11 further comprising the step of depositing a third refractory metal silicide layer on top of said second refractory metal silicide layer at a fifth flow rate of a silicon-containing reactant gas, said fifth flow rate is different than at least one of said first and said third flow rate.

15. A method according to claim 1, wherein said silicon-containing reactant gas is selected from the group consisting of $SiH_4$ and $SiCl_2H_2$.

16. A method according to claim 11 further comprising an annealing process between the deposition step of said first refractory metal silicide layer and the deposition step of said second refractory metal silicide layer.

17. A method according to claim 3, wherein said refractory metal is tungsten.

18. A method according to claim 11, wherein a refractory metal of said first or second refractory metal silicide is a member selected from the group consisting of tungsten, titanium, tantalum and molybdenum.

19. A method according to claim 18, wherein said refractory metal is tungsten.

* * * * *